US010031051B2

(12) United States Patent
Doebelin et al.

(10) Patent No.: US 10,031,051 B2
(45) Date of Patent: Jul. 24, 2018

(54) SAMPLE DEPOSITION DEVICE

(71) Applicant: CTC Analytics AG, Zwingen (CH)

(72) Inventors: Werner Doebelin, Reinach (CH);
Thomas Maetzke, Münchenstein (CH);
Chris C. E. Van Tilburg, Wemeldinge (NL)

(73) Assignee: CTC ANALYTICS AG, Zwingen (CH)

( * ) Notice: Subject to any disclaimer, the term of this patent is extended or adjusted under 35 U.S.C. 154(b) by 1 day.

(21) Appl. No.: 15/168,943

(22) Filed: May 31, 2016

(65) Prior Publication Data
US 2016/0274003 A1    Sep. 22, 2016

Related U.S. Application Data

(63) Continuation of application No. 12/541,592, filed on Aug. 14, 2009.

(30) Foreign Application Priority Data

Aug. 15, 2008 (CH) ...................................... 1290/08

(51) Int. Cl.
*G01N 1/14* (2006.01)
*G01N 35/10* (2006.01)
(Continued)

(52) U.S. Cl.
CPC ................. *G01N 1/14* (2013.01); *B08B 3/08* (2013.01); *B08B 9/023* (2013.01); *B08B 9/0325* (2013.01);
(Continued)

(58) Field of Classification Search
CPC ......... B08B 9/023; B08B 9/0325; B08B 3/08; G01N 1/10; G01N 1/14; G01N 35/1004;
(Continued)

(56) References Cited

U.S. PATENT DOCUMENTS

| 3,954,012 A | 5/1976 | Christen et al. |
| 4,347,750 A * | 9/1982 | Tersteeg ........... G01N 35/00029 |
| | | 141/130 |

(Continued)

FOREIGN PATENT DOCUMENTS

| DE | 43 14 180 A1 | 11/1993 |
| EP | 0 651 255 A1 | 5/1995 |
| EP | 1 624 301 A1 | 2/2006 |

*Primary Examiner* — Alexander Markoff
(74) *Attorney, Agent, or Firm* — Birch, Stewart, Kolasch & Birch, LLP

(57) ABSTRACT

A device for collecting a sample and for depositing the sample in a sample-receiving port of a measuring apparatus comprises a first connection element (8) with three connections for fluid, and a second connection element (7), and a hollow needle (5) for collecting and depositing the sample. A first feed line (9) for a first washing liquid is connected via a first pump to a first connection for fluid of the first connection element (8). A second feed line (10) for a second washing liquid is connected via a second pump to a second connection for fluid of the first connection element (8). A connection for fluid of the second connection element (7) is connected to the third connection for fluid of the first connection element (8), and the second connection element (7) is connected to a dosing device (1) and to the hollow needle (5). A valve (2) is arranged between the third connection for fluid of the first connection element (8) and the second connection element (7).

10 Claims, 5 Drawing Sheets

(51) Int. Cl.
*B08B 3/08* (2006.01)
*B08B 9/023* (2006.01)
*B08B 9/032* (2006.01)
*G01N 1/10* (2006.01)
*G01N 30/02* (2006.01)

(52) U.S. Cl.
CPC ........... *G01N 35/1004* (2013.01); *G01N 1/10* (2013.01); *G01N 30/02* (2013.01); *G01N 35/1097* (2013.01); *G01N 2030/027* (2013.01)

(58) Field of Classification Search
CPC ......... G01N 35/1097; G01N 2030/027; G01N 30/02
See application file for complete search history.

(56) References Cited

U.S. PATENT DOCUMENTS

| | | | |
|---|---|---|---|
| 4,656,007 A * | 4/1987 | Douchy | G01N 35/1016 221/113 |
| 5,085,832 A * | 2/1992 | Shaw | G01N 35/1083 422/547 |
| 5,474,744 A | 12/1995 | Lerch | |
| 7,219,566 B1 | 5/2007 | Maeda | |
| 2004/0175833 A1 | 9/2004 | Tatsumi | |
| 2007/0095158 A1 | 5/2007 | Maeda | |

\* cited by examiner

SAMPLE DEPOSITION DEVICE

This application is a Continuation of copending application Ser. No. 12/541,592 filed on Aug. 14, 2009, which claims the benefit under 35 U.S.C. § 119(a) to Patent Application No. CH01290/08 filed in Switzerland on Aug. 15, 2008, all of which are hereby expressly incorporated by reference into the present application.

TECHNICAL FIELD

The invention relates to a device for collecting a sample and for depositing the sample in a sample-receiving port of a measuring apparatus, comprising a first connection element with three connections for fluid, and a second connection element, and a hollow needle (5) for collecting and depositing the sample, wherein a first feed line for a first washing liquid is connected via a first pump to a first connection for fluid of the first connection element, and a second feed line for a second washing liquid is connected via a second pump to a second connection for fluid of the first connection element.

PRIOR ART

The object of such a device (also referred to as sample deposition device, autosampler or sample deposition system) is to feed samples to a measuring arrangement such as a chromatograph.

EP 0 651 255 A1 (Hoffmann La Roche) discloses an automatic pipetting device with a corresponding dosing and transport mechanism for the pipetting needle 11, which is connected via a first tube 12 and a first T-union 13 to a dosing syringe 14 (column 1, line 1). An arm of the first T-union 16 is connected to a cleaning mechanism (column 2, line 10). The pipetting device further contains a piston pump 24, which is connected via a second T-union 23 and a valve 21 to the first T-union 13 (column 2, line 16). The second T-union 23 is connected via a second valve 31 to a container 33 with cleaning liquid 34 (column 2, line 20). A control mechanism 41 controls the two valves 13, 23 and the piston pump 24 (column 2, line 24). The second valve 31 can also be designed as a check valve (column 2, line 36). Moreover, the pipetting device comprises a transport mechanism that contains a rod 52 and a transport carriage 51, by which means the pipetting needle 11 can be moved in three spatial directions (column 3, line 25). In a cleaning position, cleaning liquid is pumped through the pipetting needle into a container 38 (column 3, line 43). The tubes 22, 28, 29 are made of nondeformable material, for example of polyethylene (column 5, line 46).

DE 43 14 180 A1 (Olympus Optical) discloses a device for depositing samples in a reaction vessel (column 1, line 1). The device comprises a washing mechanism for washing a disposable unit 20, which is secured removably on the tip 20a of a sample deposition probe, and a removal mechanism for removing the disposable unit 20, and a control unit for selectively actuating the washing mechanism and the removal mechanism (column 1, line 68). The disposable unit 20 is connected to a syringe 21 (column 3, line 56). The disposable unit 20 is moved both in the horizontal plane and also in the vertical plane (column 3, line 58). A water tank 11 and a tank 12 with washing agent are provided, and also pumps 13, 14 for introducing the water and the washing agent into the wash tank 19 and into the syringe 21, respectively, which purpose is served by the valves 15-18 (column 4, line 32). In washing mode, the disposable unit 20 is washed externally in a wash tank 19 and is subsequently washed internally by washing agent being sucked in by means of the syringe 21 and then ejected through the disposable unit 20 (column 4, line 41).

EP 1 624 301 A1 (Shiseido) discloses a sample injection apparatus for an LC (liquid chromatograph) [0001]. The autosampler device comprises a needle 10, a syringe 11, a pump for the cleaning liquid 12, a valve 13, a sample container 14, an injection valve 15, a loop 16, a cleaning device 17, a cleaning agent container 18, and a device for transporting the needle [0051]. The cleaning liquid in the container 18 is pumped continuously to the cleaning device 17 or to the needle 10 by means of the pump 12, depending on the setting of the valve 13 [0051]. The needle 10 is inserted at the injection port 19 of the injection valve 15, which injection port 19 is connected to the loop 16, in order to inject the sample or the cleaning agent [0051]. Directly before the sample is injected, the needle 10 is washed externally in a cleaning device 17, and the sample is then injected through an injection port 19 into a loop 16, after which a valve is switched such that the sample enters the column 105 [0004]. Directly after the injection of the sample, the inside of the needle 10 is washed by means of cleaning liquid being flushed through the needle 10 [0007]. For rewashing after the injection, cleaning liquid is drawn into the needle 10 at a cleaning port 24 and is repeatedly drawn in and ejected at the injection port 19 of the injection valve 15 in order also to clean the sample injection path in the injection valve 15, wherein the injection port 19 is connected to the waste container 23, but not to the loop, and wherein two or more cleaning ports 24 can be used [0008]. Instead of drawing up and ejecting cleaning liquid, it is also possible for the needle 10 to be cleaned by means of ultrasound [0012], [0025]. In FIG. 12, the needle 10 makes up part of the line 25, such that two ports of the injection valve 15 can be connected, and the needle 10 can be decoupled for sample collection and for cleaning and can be guided to the sample container 14 or the cleaning device 17, 17', respectively, by means of a transport mechanism [0061].

U.S. Pat. No. 7,219,566 B1 from Shimadzu discloses a sample deposition system. The latter comprises an injection valve (4), which is designed as a high-pressure rotary valve with multiple inlets/outlets. It also comprises a low-pressure valve (5), which is likewise designed as a rotary valve with multiple inlets/outlets. A hollow needle (10) is mounted in a movable manner and can travel between the sample bottles (11), the wash station (8) and the injection port (9) on the injection valve (4). To collect the sample with the hollow needle, a metering pump (6) which is fixed, i.e. not movable, in contrast to the hollow needle, is connected to the hollow needle with the low-pressure valve, and the sample is aspirated into what is called a sample loop (7) and temporarily stored there. As the hollow needle moves back and forth, this sample loop is moved, for which reason it has to be of a flexible design. Because of different degrees of expansion of the sample loop (for example caused by temperature or pressure fluctuations, etc.), this can have a negative impact on the dosing accuracy and the dosing reproducibility. Moreover, the parts of the device contaminated by the sample are cleaned by washing liquid (cleaning solution—FIG. 4) being aspirated by the metering pump via the low-pressure valve and, after switching of the low-pressure valve, being emptied into the wash station, where the hollow needle is immersed for cleaning. Accordingly, the metering pump has to be filled repeatedly with washing liquid if a quantity of washing liquid is needed that exceeds the volume of the metering pump. Apart from taking a long time, this also results in considerable wear of the parts. Furthermore, the hollow needle has to be moved in each case to the wash station for cleaning.

DETAILED DESCRIPTION OF THE INVENTION

With measuring instruments (detectors) becoming ever more sensitive, there is a need for sample deposition systems that are much better than conventional systems in terms of cross-contamination, reproducibility, speed and long life (robustness).

The devices according to the prior art have the disadvantage that the injection needle cannot be efficiently cleaned.

Furthermore, cross-contamination of the sample material can only be partially avoided. Finally, the sample volume to be collected cannot be reproduced in an optimal manner.

Therefore, the object of the invention is to make available a device belonging to the technical field mentioned in the introduction and also a corresponding cleaning method, which device and method ensure the least possible cross-contamination with at the same time a high degree of accuracy, speed and long life.

The object is achieved by the features of Claim 1. According to the invention, a connection for fluid of the second connection element is connected to the third connection for fluid of the first connection element, and the second connection element is connected to a dosing device and to the hollow needle, and a valve is arranged between the third connection for fluid of the first connection element and the second connection element.

The dosing device is connected to the hollow needle in order to allow the sample to be collected and deposited through same.

This design not only permits rapid and simple flushing of the hollow needle and of the parts of the device that come into contact with the hollow needle and/or with the sample, for example the injection valve through which the sample is delivered to the measuring apparatus, but also permits flushing of the hollow needle as long as the latter is still in the injection port of the injection valve, i.e. without first having to remove the hollow needle from the injection port.

Additionally, the arrangement, according to the invention, of the individual parts of the device permits substantially uninterrupted or continuous cleaning of the device, since washing liquid can be pumped through the hollow needle by the first and/or second wash pump until the needle is cleaned or, finally, a supply of washing liquid is exhausted. Naturally, in the latter case, depending on the design of the device, a reservoir of washing liquid can also be refilled during operation.

By activating the pumps, it is possible to clean the device, or parts thereof, very quickly and simply and with any desired quantities of two different washing liquids (solvents), for example an aqueous and an organic washing liquid, without a valve having to be switched for this purpose. Additionally, the hollow needle and the injection valve can be rinsed through while the hollow needle rests in the injection port, without the hollow needle having to be moved.

By forming a valve between the third connection for fluid of the first connection element and the second connection element, it is possible to avoid a backflow of a fluid (sample, washing liquid) in the direction of a feed line for a washing liquid. In particular, the device can be kept particularly simple by this means since, apart from the sample port to the measuring apparatus, no further valve is necessarily required. Thus, the several washing liquids can be controlled by just one valve, by activating the corresponding pump and opening the valve. A controlled valve can be used in order to actively avoid the backflow.

The pumps are preferably designed such that they are able to continuously convey washing liquids. The pumps can be designed as peristaltic pumps, diaphragm pumps, rotary piston pumps, rotary vane pumps, gear pumps or as piston pumps, in particular as axial piston pumps or reciprocating piston pumps.

The hollow needle can be designed for this purpose as a cylindrical hollow element, in particular as a cannula, the cannula having an outlet opening that can be straight and/or beveled. In this way, the hollow needle can be easily pushed through a membrane, for example. Furthermore, disposable attachments can also be used.

The valve is preferably designed as a solenoid valve, in particular as a solenoid valve with a nominal volume of less than 0.1 ml. A solenoid valve is a valve that is actuated by an electromagnet. The use of a solenoid valve has several advantages:
1. Solenoid valves are controllable and can therefore be switched independently of a line pressure.
2. Solenoid valves have short switching times, in particular with switching times in the range of milliseconds being achievable.
3. Switching frequencies in the kilohertz range are possible.
4. Solenoid valves are available in compact format.
5. Solenoid valves require little maintenance.

As an example of a solenoid valve design, reference is made here to the flipper solenoid valves from the Bürkert company, which are distinguished by particularly small dimensions (4.5 mm wide and 38.5 mm deep), small internal volume (0.03 ml) and by a switching frequency of up to 80 Hz. However, a large number of similar solenoid valves that can also be used are known to a person skilled in the art. In particular, larger or smaller solenoid valves can also be used if space is not limited or if a more inexpensive design is wanted. Furthermore, a different internal volume can also be chosen depending on the application, although a smaller internal volume is preferable in principle. The switching frequency can also be less than 80 Hz, without having to accept any appreciable loss of accuracy. However, switching frequencies of 80 Hz or higher are of course preferred.

Furthermore, the device can also have another valve arranged between the third connection for fluid of the first connection element and the second connection element. For example, a check valve for avoiding a backflow of a fluid (sample, washing liquid) in the direction of a feed line could be formed, in particular as a spring-loaded ball-type or diaphragm-type check valve. The pressure of the valve spring is typically less than 1 bar, preferably approximately 0.3 bar. This pressure must be overcome by the wash pump in order to pump the washing liquid through the check valve. However, the pressure of the spring must not be too low either, because the valve must not be opened by a slight underpressure on the output side, as can arise from a piston stroke of the dilutor (which is also referred to below as syringe). These problems can be eliminated by using a controlled valve, in particular a solenoid valve.

This solenoid valve replaces the rotary valve (5) provided in the prior art according to U.S. Pat. No. 7,219,566 B1.

The second connection element preferably comprises three connections for fluid, wherein a first connection for fluid of the second connection element is connected to the valve, a second connection for fluid of the second connection element is connected to the dosing device, and a third connection for fluid of the second connection element is connected to the hollow needle. The valve is closed in a first state, as a result of which for example, upon activation of the dosing device, a liquid can be pumped through the hollow needle via the second connection element, without the liquid coming into contact with a washing liquid. In a second state, the valve is opened. In this state, the dosing device is typically not activated, because washing liquid could be aspirated through the second connection element by a suction action (Bernouilli principle) of the actuated dosing device, especially if the pumps do not have a backflow safety mechanism. In the second state, that is to say with the valve open, cleaning is typically carried out. By means of the first and/or the second pump, washing liquid is pumped through the first connection element via the valve, through the second connection element and through the hollow needle. By means of this arrangement, the dosing device be decoupled during a cleaning procedure. It is thus possible, by simple design means, to prevent washing liquid from entering the dosing device.

Furthermore, the second connection element can also be formed by the dosing device itself or by a part thereof. For this purpose, the outlet of the valve would connect directly to the dosing device, that is to say a fluid connection would be provided between the valve and the dosing device. The hollow needle would then be connected separately to the dosing device via a further fluid connection. However, this would have the disadvantage that the dosing device would necessarily be contaminated with washing liquid.

The dosing device preferably comprises a syringe body and a ram and can be actuated in particular by motor. For this purpose, the dosing device comprises a linear guide. The ram can for this purpose comprise, for example, a toothed rod in its longitudinal direction, which toothed rod cooperates with a toothed wheel of a motor, in particular of a stepping motor. In this way, the ram can be moved in its longitudinal direction by means of actuation of the motor, and particularly precise strokes can thus be executed, as a result of which a volume to be dosed can be accurately set. Moreover, the motorized operation of the dosing device also permits control by means of a computer, as a result of which more complex sequences of the device can also be controlled and in particular automated. Instead of the ram, the syringe body too can be moved by means of a linear guide. The syringe can in principle be oriented in any desired manner. However, it is preferably vertical, with an outlet opening arranged at the bottom.

Instead of motorized actuation, a pneumatic or manual actuation of the dosing device is also conceivable. A pneumatic drive is in particular conceivable if the volume to be dosed is not regularly changed. In this case, the dosing device can have an abutment for the pneumatics, which limits a movement of the pneumatics and thus defines the volume to be dosed. The abutment can be designed to be adjustable, such that different volumes can be dosed.

The dosing device is preferably exchangeable and in particular can be replaced by dosing devices of different volumes. A particularly versatile device is achieved in this way.

Typically, the volumes to be analyzed are not always the same. Depending on the concentration or nature of the substance to be tested, a different volume of sample material is therefore tested. By means of the exchangeable dosing device, it is possible, for example, for different syringes, including syringe body and ram, with different maximum volumes to be made available, such that the device can be adapted to the respective measurements and thus to the volumes that are to be dosed. In particular, a relative precision of the volume to be dosed can thus be maintained even for different volumes.

Alternatively, in particular for use in routine analyses, replaceable dosing devices can be dispensed with, and in some cases the device can thus be produced more cost-effectively. In doing so, however, account would possibly have to be taken of the loss of the abovementioned advantages, in particular the loss of versatility of use.

The hollow needle, the dosing device and the valve are preferably secured on a movable support. That is to say, the hollow needle, the dosing device and the valve are spatially fixed relative to one another, such that they are moved jointly upon movement of the support. As a result of the mutual spatial fixing, in particular of the hollow needle and of the dosing device, no flexible fluid line has to be provided between the hollow needle and the dosing device. This would have the disadvantage that, during travel of the hollow needle between the sample containers and the injection valve, the flexible fluid line would be bent, and uncontrollable changes in volume could arise as a result. This in turn would have a negative influence on the reproducibility of sample delivery in sample-receiving ports of measuring apparatuses. In this embodiment, therefore, only the feed lines for the washing liquids are flexible.

The injection valve and the sample containers could also be designed to be movable. However, the problem would only be apparently solved by this, since connecting elements between the injection valve and the measuring apparatus would have to be made flexible. In addition, the design complexity would be considerably greater.

The support is preferably movable in three different spatial directions. This is particularly advantageous if the sample containers are arranged in a plurality of rows. The mobility of the support can be obtained using three linear guides, which are driven by stepping motors, for example. The drive can be effected by means of a combination of toothed rods and drive pinions or by means of device like a cable pull. However, mounting on an articulated robot arm is also conceivable.

If the sample containers are arranged in only one row, i.e. if typically only a few sample containers are used, mobility in two spatial directions may suffice, in which case the two spatial directions are oriented in a vertical plane and the sample containers are arranged horizontally in the same plane.

The two connection elements are preferably secured on the movable support. Securing the two connection elements on the movable support has the effect that, during a movement of the support, they too are moved together with the hollow needle, the dosing device and the valve. Furthermore, a volume between the two connection elements is thereby kept small, as a result of which it is possible to switch more quickly between the two washing liquids, without a relatively large quantity of the previous washing liquid having to be flushed through.

Accordingly, the hollow needle, the valve, the connection elements and the dosing device do not have to be moved relative to one another, such that an improved dosing accuracy and dosing reproducibility can be achieved.

That is to say, the only connection between the components of the device that are movable with the support and the components that are not movable is formed by the feed lines for the washing liquids. These feed lines are accordingly flexible.

The first connection element can also be arranged fixed in position, as a result of which only one flexible line would have to be routed to the valve. However, this would have the disadvantage that the volume between the two connection elements would be greater and, consequently, when switching between the washing liquids, a greater time interval would elapse before the other washing liquid reaches the hollow needle. Moreover, this can result in the two washing liquids mixing together over a greater volume.

Preferably, a first fluid connection between the connection for fluid of the second connection element and the dosing device and/or a second fluid connection between the second connection element and the hollow needle is/are made of a rigid material, in particular of a metal or a rigid plastic. A particularly high degree of precision and reproducibility of the volumes to be dosed is thereby achieved, since the fluid connections cannot deform. In order to obtain a particularly compact, stable and structurally simple embodiment, the fluid connections can be formed as bores in a solid element made of metal or plastic. This also has the advantage in particular that the connection sites remain leaktight even when subjected to high pressure.

Finally, this embodiment is also preferable from the esthetic point of view.

Of course, it is also possible to use flexible connections. The advantage of doing so is that these are easier to replace and are commercially obtainable as standard parts.

The second connection element is preferably connected to the hollow needle via a third fluid connection, wherein the third fluid connection is advantageously exchangeable in order to permit variation of a sample volume. In this way, the washing liquid can be pumped directly through the hollow needle without entering the dosing device. The third fluid connection can also be designed as a so-called load loop into which the sample material is sucked. This has the advantage that the sample material does not enter the dosing device. The third fluid connection or load loop is designed to be exchangeable, in particular if the dosing device is also designed to be exchangeable. Thus, the volume of the third fluid connection or load loop can be adapted to the maximum volume of the dosing device. The larger the dosing device, i.e. the greater the maximum volume of the dosing device, the greater is the third fluid connection or load loop, in which context the maximum volume of the dosing device is to be understood as meaning the maximum volume that can be taken up, for example by the syringe body thereof.

The third fluid connection can also be connected to the dosing device and to the hollow needle, in which case, however, the washing liquid would have to be pumped through the hollow needle via the dosing device.

The load loop and the hollow needle are preferably designed in one piece. When using different sample volumes, the diameter of the hollow needle also has to be adapted in some circumstances to the sample volume. If the load loop is to be adapted to a new sample volume, it may possibly be necessary to replace the hollow needle too. This is particularly the case if the sample volumes differ greatly, for example if changing from a microliter range to a milliliter range. Thus, simplified adaptation is achieved by means of a one-piece design of load loop and hollow needle.

The hollow needle and the load loop can also be present separately, which permits more flexible adaptation to the circumstances.

The sample is preferably liquid. Solid samples are preferably dissolved in a suitable solvent and in turn used as liquid samples.

Alternatively, the sample can also be gaseous, in which case, however, particular attention has to be paid to the leaktightness of the seals and of the transitions between the fluid connections.

The measuring apparatus preferably comprises a chromatograph, in particular a liquid chromatograph.

The device can also be used for other measuring methods which are sufficiently familiar to a person skilled in the relevant art and in which a defined volume of fluid has to be measured in advance. In particular, the device can also be used for carrying out sample preparation. For example, the device can be used successfully in microbiology, in genetics or similar fields where very small volumes have to be measured with a high degree of precision. Thus, for example, cells could also be inoculated or very small quantities of substances, in particular liquid substances, could be mixed.

In order to clean the hollow needle, the device preferably comprises a wash module with a waste tank and at least one immersion position. For a washing operation, the hollow needle can thus be guided over the waste tank and, with the valve open, the first and/or the second washing liquid can be pumped through the hollow needle into the waste tank by means of the corresponding pump(s). In this way, the hollow needle can be cleaned continuously without being subjected to a series of dilutions, which would take place if the washing liquid were drawn up and discharged several times by the dosing device as in the prior art. The immersion position is designed as a vessel with an overflow, and the overflow can be routed into the waste tank. In this way, all of the washing liquid can be collected in a single tank. The hollow needle is inserted into the immersion position, and a washing liquid is then pumped through the hollow needle. In this case, there is the possibility of the vessel being filled with the washing liquid to the extent that the hollow needle is immersed in the same washing liquid. However, the immersion position can also already be filled with washing liquid in advance. This has the effect that the hollow needle can also be washed on the outside. For this purpose, the immersion position can also be subjected to ultrasound, in order to make the cleaning process more efficient. A person skilled in the art will also know of other possible ways by which the cleaning can be optimized.

Disposable hollow needles can also be used, making cleaning unnecessary. The device can be configured such that, in a disposal mode, the hollow needle can be discarded after use and, in a wash mode, the hollow needle can be cleaned after use, in particular after each use. This is particularly of interest when especially high demands are placed on the cleanliness of the hollow needle, for example if cross-contamination is to be avoided.

The device preferably comprises an injection valve with an injection port, in which case, with the hollow needle positioned in the injection port, the sample can be discharged via the injection valve into the sample-receiving port of the measuring apparatus. This is particularly advantageous if the measuring apparatus comprises a liquid chromatograph or a high-pressure liquid chromatograph.

Moreover, the sample material can also be discharged into a vessel or made available for another type of further processing.

The device preferably comprises a sample holder for the provision of samples. For this purpose, the sample holder comprises a number of positions for placing sample containers. The sample holder typically has a rectangular base surface, with the positions being arranged in parallel rows.

A staggered arrangement of the rows is also possible. This has the advantage that the sample containers can be arranged in a way that saves space.

Alternatively, the sample holder can also be omitted. In the method for cleaning a device used to collect a sample and to deposit the sample in a sample-receiving port of a measuring apparatus with a hollow needle, a first feed line for a first washing liquid, a second feed line for a second washing liquid, and a dosing device, the first washing liquid is pumped by the first wash pump and/or the second washing liquid is pumped by the second wash pump past the dosing device and through the hollow needle.

Further advantageous embodiments and combinations of features of the invention will become evident from the following detailed description and from the totality of the patent claims.

DETAILED DESCRIPTION OF THE INVENTION

Brief Description of the Drawings

In the drawings used to explain the illustrative embodiment.

In principle, identical parts in the figures are provided with the same reference signs.

WAYS OF IMPLEMENTING THE INVENTION

Figure 1:
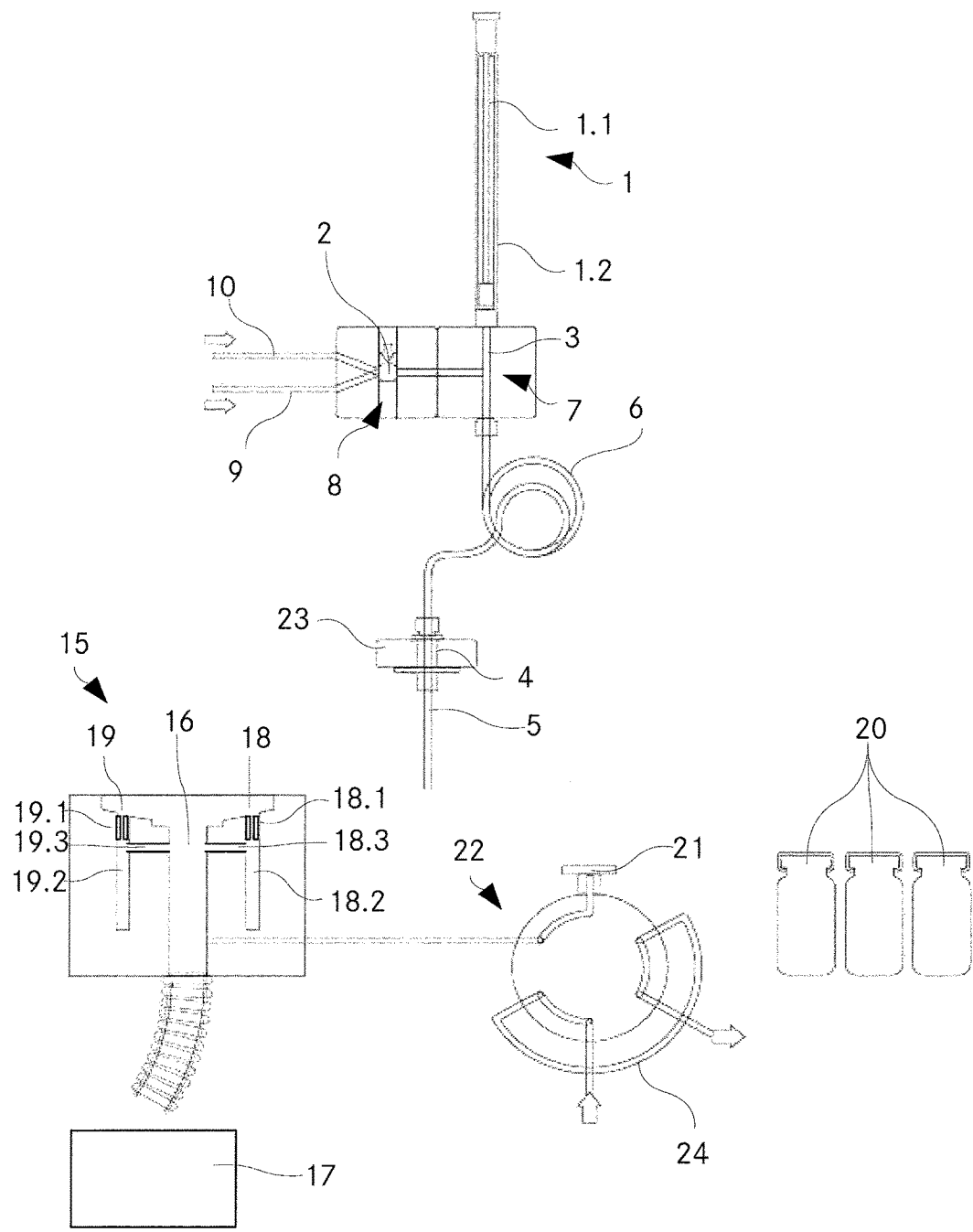
FIG. 1 shows a schematic view of a first illustrative embodiment of a device according to the invention.

FIG. 1 shows a schematic view of a first illustrative embodiment of a device according to the invention.

The solenoid valve 2, with an inlet and an outlet, the T-pieces 7 and 8 and the dosing device form a unit. In the present embodiment, this unit is formed from a workpiece, for example of plastic or metal. The T-pieces 7, 8 are realized as bores in the workpiece. The first T-piece is connected via two connections for fluid, with fluid lines 9, 10, to two respective pumps which can convey washing liquids, for example organic and inorganic washing liquids, from corresponding containers (not shown).

A third connection for fluid of the first T-piece 8 is connected to the inlet of the solenoid valve 2. It will be seen from FIG. 1 that the solenoid valve itself is to an extent the third connection for fluid of the first T-piece.

The outlet of the solenoid valve 2 is connected to the second T-piece 7. Furthermore, the second T-piece 7 is connected to the dosing device 1 via a dilutor line, which is also formed as a bore in the workpiece. The dosing device 1 comprises a syringe body 1.2 and a ram 1.1 that is arranged displaceably in the syringe body 1.2 in the longitudinal direction. In the present embodiment, liquid is drawn up and discharged by movement of the ram 1.1 of the dosing device 1, although this can also be done by displacement of the syringe body 1.2 while the ram 1.1 is fixed in position.

A third connection for fluid of the second T-piece 7 is connected to the hollow needle 5 via a load loop 6 and the needle adapter 4. In this way, by means of the dosing device, a sample volume can be aspirated through the hollow needle 5 into the load loop 6. The load loop 6 is dimensioned in terms of its volume in such a way that the sample volume cannot enter the dosing device 1. For this purpose, the dosing device 1 and the load loop 6 are matched to each other to an extent.

The hollow needle 5 is connected by the needle adapter 4 to a needle adapter holder 23. The two T-pieces 7, 8, the solenoid valve 2, the dosing device 1, the load loop 6, the needle adapter 4, the hollow needle 5 and the needle adapter holder 23 are arranged in a fixed position relative to one another on a support 25 (shown in FIG. 2) which can be displaced by means of three linear guides oriented perpendicularly to one another (not shown). To permit this, the fluid connections 9, 10 are designed to be flexible, for example in the form of plastic tubes. In this way, containers of washing liquid can be arranged fixed in position.

FIG. 1 also shows a sample holder 20 for provision of sample material that is to be tested. Before sample material is drawn up, air is aspirated. By means of the support 25 (shown in FIG. 2), the hollow needle 5 can be guided to the sample holder 20 such that, with the solenoid valve 2 closed, sample material is drawn up through the hollow needle 5 into the load loop 6 by means of the dosing device 1. Thereafter, air is aspirated into the hollow needle 5 by means of the dosing device 1. In this way, the sample material is enclosed between two air bubbles, thereby ensuring that the sample material cannot be contaminated with washing liquid. Depending on the application, however, it is also possible to dispense with the air bubbles. This is the case, for example, if the sample material is sensitive to air or if, for example because of the viscosity or other properties of the sample material, mixing with the washing liquid cannot take place to an extent that would influence the measurement results. More sample material is generally aspirated than is finally used for the analysis in the measuring apparatus. However, it is also possible, for example in HPLC (high-pressure liquid chromatography), for a washing liquid to at the same time represent the mobile phase, as a result of which exactly the volume of sample material to be used for the analysis is aspirated through the dosing device 1.

FIG. 1 also shows a wash module 15 with two immersion positions 18, 19 and an outflow channel 16, which leads into a waste tank 17. The two immersion positions 18, 19 are designed as vessels which are open at the top and which have an overflow into the outflow channel 16. By means of the support 25 (shown in FIG. 2), the hollow needle 5 can be inserted into the outflow channel 16. By means of the support 25, the hollow needle 5 can be guided into one of the immersion positions 18, 19. With the solenoid valve 2 open, washing liquid can now be pumped through one or both fluid connections 9, 10 and through the two T-pieces 7, 8, such that the washing liquid flushes through the load loop 6 and the hollow needle 5. The pumps are designed such that they are able to convey washing liquid continuously. The washing liquids then flows into the corresponding immersion position 18, 19 and overfills this, whereupon the washing liquid passes via the overflow and through the outflow channel 16 into the waste tank 17. By means of the support 25, the hollow needle 5 can also be inserted into the outflow channel 16, such that residues of the sample material, which is located in the hollow needle 5 or in the load loop 6, can be ejected directly into the waste tank 17 by means of the pumps. In this way, the outside of the hollow needle 5 is not unnecessarily contaminated with sample material.

When more powerful wash pumps are employed, which afford a further saving in time as regards the duration of the wash cycle, simple wash cavities (immersion positions 18, 19) in the form of bores create the problem of washing liquid squirting back. Therefore, a wash station is designed such that two rod-like inserts (immersion positions 18, 19) are arranged with different bore diameters 18.1, 18.2 and 19.1, 19.2, respectively. At the top end, they each have a narrow inlet bore 18.1, 19.1, through which the needle only just fits and, in the lower part, they each have a slightly larger bore 18.2, 19.2. Lateral outlet bores 18.3, 19.3 at the level of the transition of the two bore cross sections 18.1, 18.2 and 19.1, 19.2, respectively, serve to ensure that the wash stream can flow out laterally at this position and flow into the outflow channel. Depending on the power of the wash pump, however, it is also possible to dispense with the different bore cross sections, in which case the immersion positions 18, 19 can have a shape of a straight prism, in particular a tube shape.

FIG. 1 also shows an injection valve 22, which comprises an injection port 21 and a loop 24. The injection port 21 of the injection valve 22 comprises a valve and can therefore be switched between loop 24 and waste tank. In a first position, liquid fed into the injection port 21 is conveyed directly into the waste tank 17. In a second position, liquid fed into the injection port 21 is conveyed into the loop 24.

By means of the support 25 (shown in FIG. 2), the hollow needle 5, which together with the load loop 6 comprises the sample material, enclosed by two air bubbles, and is washed on the outside can be inserted into the injection port 21 of the injection valve 22. With the solenoid valve 2 still closed, and in the first position of the injection port, a first volume is now ejected directly into the waste tank by means of the dosing device 1. The first volume comprises the last air bubble taken up and some of the collected sample material. Thereafter, the injection port 21 is switched to the second position and thus connected to the loop 24. Now, by means of the dosing device, the exact volume of sample material needed for the analysis is pumped into the loop 24, with a residue of sample material still remaining in the hollow needle 5 and possibly also in the load loop 6. The injection port 21 is switched back to the first position. The rest of the sample material and the second air bubble are now ejected through the hollow needle 5 in the direction of the waste tank 17 by means of the dosing device 1. In order to eject the remaining sample material completely from the injection valve 22, the solenoid valve 2 is now opened and, by means of the pumps, first and/or second washing liquid is pumped through the hollow needle 5 into the injection port, whereupon the injection port 21 in the first position conveys the washing liquid into the waste tank 17. During this procedure, the sample material can be pumped from the loop 24 to the measuring apparatus by means of a further pump.

By virtue of the fact that only a central part of the sample material sucked out through the hollow needle 5 and the load loop 6 is used for the analysis, it is possible to ensure that no sample material contaminated with washing liquid enters the measuring apparatus, as a result of which the measurement results become more reproducible and more accurate.

By means of the support 25 (shown in FIG. 2), the hollow needle 5 can be guided from the injection port 21 to the second immersion position 19 and rinsed with the second washing liquid, in order to wash the needle inside and outside. Thereafter, the hollow needle 5 is once again guided by means of the support 25 into the injection port 21, where it is rinsed with the first washing liquid. The injection port 21 is located in the first position, such that the washing liquid enters the waste tank 17. Finally, the hollow needle 5 is guided by means of the support into the first immersion position 18 and rinsed with the first washing liquid and washed on the outside. The washing liquid passes via the overflow and through the outflow channel 16 into the waste tank 17. The solenoid valve 2 is now closed, and the hollow needle 5 is transferred by means of the support 25 to a rest position, until the next cycle starts.

Figure 2:
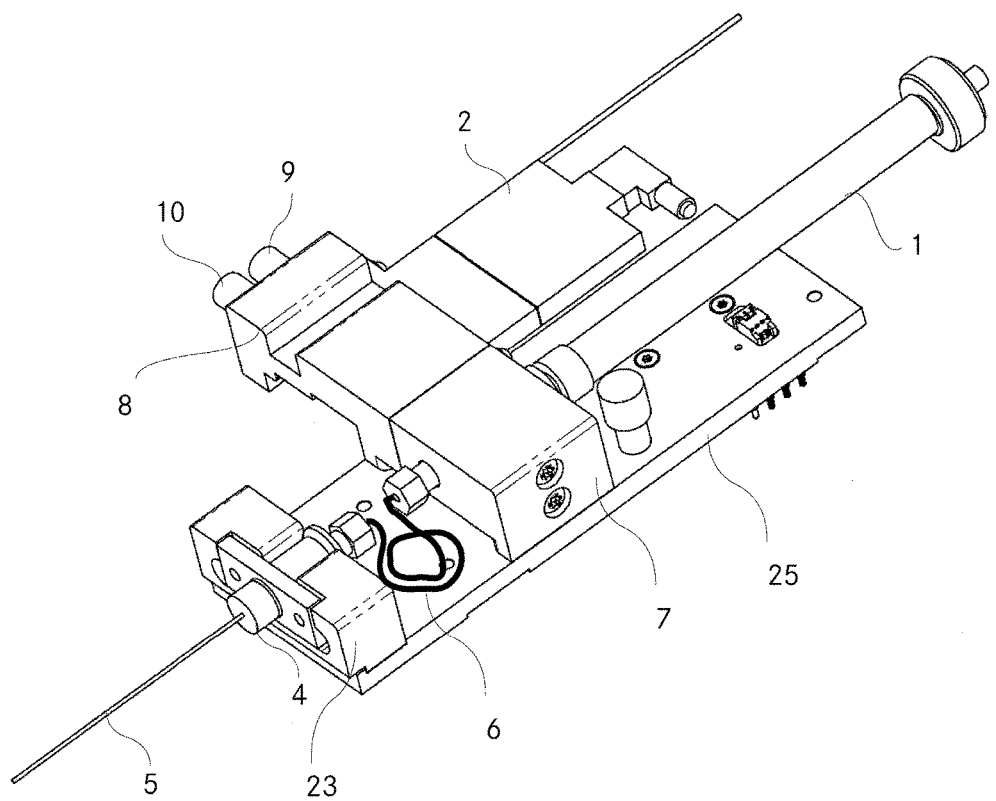
FIG. 2 shows a schematic oblique view of the movable part of the device according to the invention.

FIG. 2 shows a more detailed schematic oblique view of the movable part of the device according to the invention, which has the two fluid connections 9, 10, the solenoid valve 2, the two T-pieces 8, 9 (not explicitly shown), the dosing device 1, the load loop 6, the hollow needle 5, the needle adapter 4 and the needle adapter holder 23. The needle adapter 4 and/or the needle adapter holder 23 are resilient. In this way, the hollow needle can be sealed tightly in the injection port 21 under the resiliency pressure, such that liquid (sample material or washing liquid) ejected through the needle 5 cannot escape between the hollow needle 5 and the injection port 21. FIG. 2 also shows a support 25 to which all of the abovementioned parts are connected either directly or indirectly. For this purpose, the support 25 is designed principally as a rectangular plate which, on the rear face, has a holding device for one or more linear guides, said support being movable. Depending on the intended use, the support can typically be moved, by means of a linear guide, in the longitudinal direction of the needle or, by means of an additional linear guide, can be moved in one plane or, by means of all three linear guides, can be moved in three dimensions. The load loop 6, the needle 5 and the dosing device 1 are designed to be exchangeable.

Figure 3:
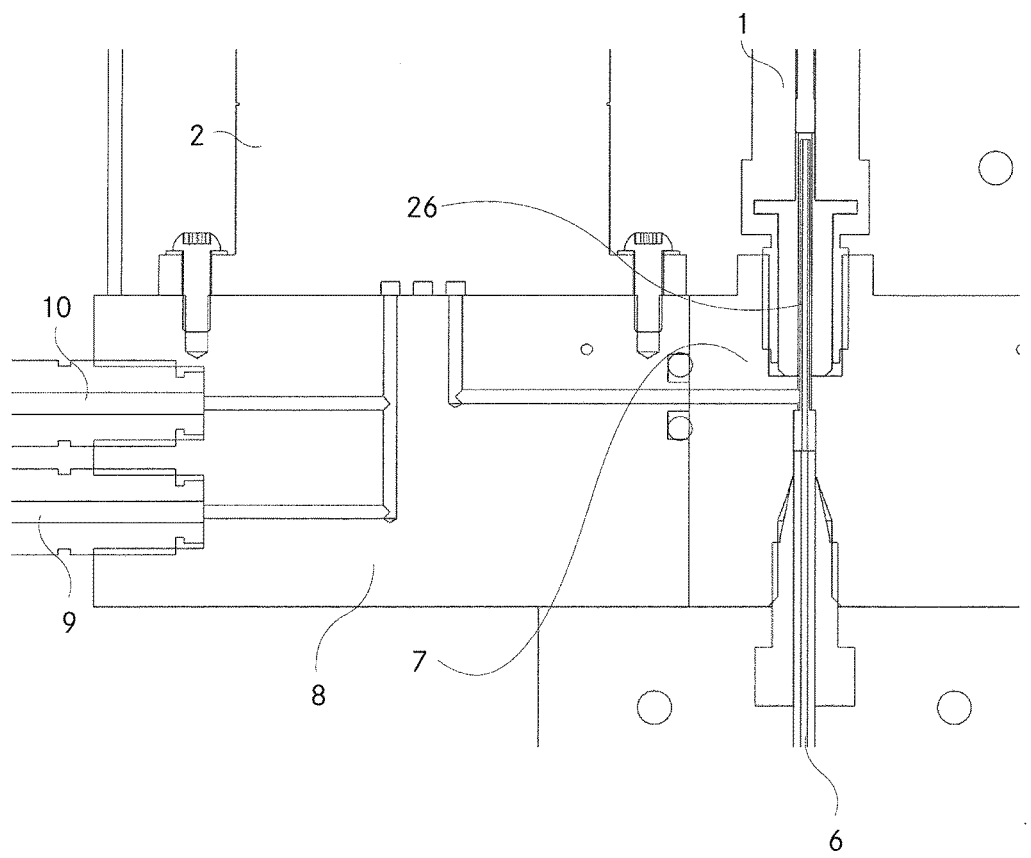
FIG. 3 shows a section through the movable part of the device according to the invention.

FIG. 3 shows a section through the movable part of the device according to the invention, essentially according to FIG. 2.

In the present embodiment, the T-pieces 7 and 8 are each formed from one workpiece. The T-piece 8 has three communicating bores, of which two bores are connected to fluid connections 9, 10, while a third bore is connected to the inlet of the solenoid valve 2. The same workpiece has two other communicating bores, of which a first bore is connected to the outlet of the solenoid valve 2, while the second bore is in communication with the second T-piece 7. The second T-piece 7 is also formed from one workpiece and has three communicating bores, of which a first bore is in communication with the first T-piece 8, a second bore forms a connection element for the dosing device 1, and a third bore forms a connection element for the load loop 6, which in FIG. 3 is only shown as an attachment. The two workpieces are screwed together in such a way that the connection between the two T-pieces 7, 8 is leaktight. The formation of the two T-pieces 7, 8 from individual workpieces is advantageous, because all the fluid connections can in this way be accessed through straight bores.

To ensure that gas bubbles, which may form as a result of degassing in the mixing zone of two liquids, are not able to settle in the blind zone 3 of the connection element 7 (FIG. 1), and to ensure that the washing liquid reaches and flows through every hollow volume in the connection element 7, a cannula insert 26, which carries a holding cylinder at the lower end, is inserted into the T-piece of the connection element 7. The washing liquid is thus initially routed from the T-piece along the outside of the cannula insert 26 to a point below the dilutor and from there through the interior of the cannula insert 26 down to the fluid connection of the load loop 6. This coaxial construction permits two opposite directions of flow within a narrow bore cross section through a blind passage.

Of course, instead of the workpieces provided with bores, it is also possible to use lines made of plastic or metal.

In the present embodiment, the diameters of the bores (lines) of the two T-pieces 7, 8 are each 1 mm. A bore has a length of between 5 mm and 30 mm. The connecting line between the second T-piece 7 and the dosing device measures 0.41 mm, and the internal diameter of the load loop 6 is 0.5 mm. The length of the load loop 6 is variable, that is to say the load loop 6 is exchangeable and is adaptable to the given circumstances. The same applies to the dosing device 1. The latter, in the present embodiment, has a diameter of 1 mm or 0.72 mm and a length (maximum stroke volume) of 19.5 mm. All of the dimensions are to be understood only as examples. An increase or decrease in the size of the individual fluid connections does not have to be done proportionally. In particular, for an LC (liquid chromatograph), the whole device can have substantially greater dimensions. The lines/bores can in this case have diameters of several millimeters and the dosing device 1 can have a displacement volume of several milliliters.

However, the lengths of all the bores are to be kept as short as possible, so as to achieve a small overall volume. This is important for being able to switch quickly between the two washing liquids. The reason for this is that, when switching between the washing liquids, the so-called dead volume (the entire volume of the lines starting from the first T-piece 8) first has to be freed of the "old" washing liquid using the new washing liquid.

Figure 4:
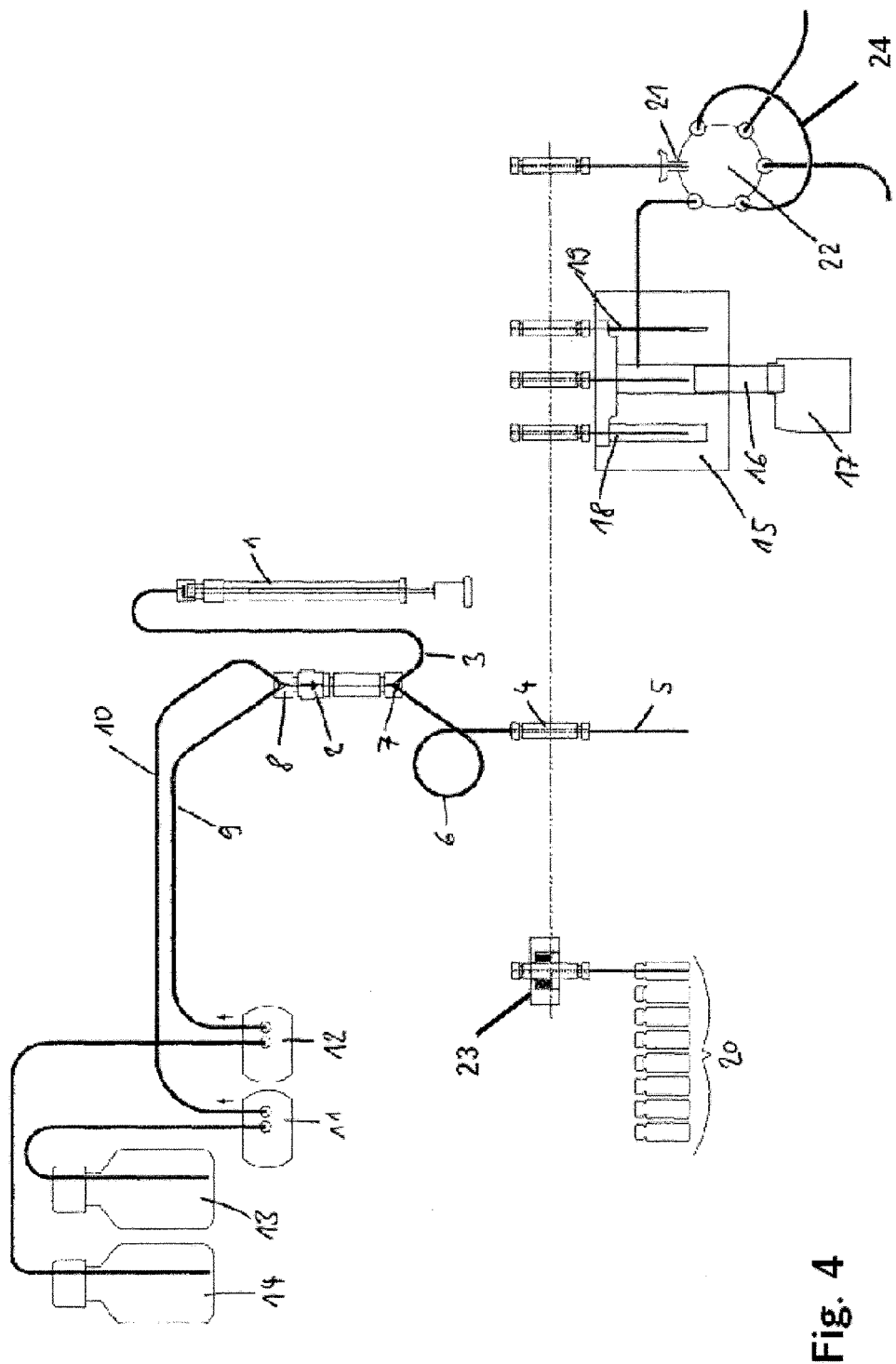
FIG. 4 shows a schematic view of a second illustrative embodiment of a device according to the invention.

FIG. 4 shows a schematic view of a second illustrative embodiment of a device according to the invention.

The device is based on an XYZ unit in which, as regards the choice of material and the rinsing volume, it is relevant which components are moved with the XYZ arm and which components are fixed in position. The wash lines 9 and 10 are flexible and connect the fixed components (reference signs 11-22) to the moved components (reference signs 1-8). The moved components 1-8 are located on the Z-axis. Thus, the wash module 15, the sample holder 20 and the injection port 21 on the injection valve 22 can be brought to the hollow needle 5. At the inlet and outlet of the valve 2, there is in each case a T-piece 7 or 8 which, at the inlet, connects the wash lines 9 and 10 and, at the outlet, connects the dilutor line 3 to the load loop 6.

The valve 2 decouples the dilutor 1 (dosing device 1) from the wash lines 9 and 10 and thus from the wash pumps 11 and 12. The suctioning and dosing of the samples is effected exclusively via the hollow needle 5 with the dilutor 1. The volume of the load loop 6 is such that, even at the maximum stroke of the dilutor 1, the sample cannot reach as far as the T-piece 7 at the outlet of the valve 2. The cleaning typically takes place with two different solvents 13 and 14 (aqueous/organic) by means of the wash pumps 11 and 12 which, via the wash lines 9 and 10, are forced through the valve 2, through the load loop 6, through the needle adapter 4 and through the hollow needle 5.

By means of this arrangement of the individual components, the area contaminated with sample can be rinsed quickly and with different solvents (cleaning agents, washing liquids) 13 and 14, in particular continuously rinsed, without the dilutor 1, in particular without contaminating the dilutor 1. When the needle is moved into the immersion positions 18 and 19 of the wash module 15, the outer area of the hollow needle 5 contaminated with sample can also be cleaned. When the hollow needle lies in the injection port 21 of the injection valve 22, it is possible, on the one hand, for a sample to be dosed with the dilutor 1, and, on the other hand, the injection port 21 and the injection valve 22 can be rinsed and cleaned with the washing solvents 13 and 14 by means of the wash pumps 11 and 12. The washing solvents flow through the outflow channel 16 into the waste tank 17.

The items with reference signs 1-8 are mounted directly on the Z-axis. The volume of the wash lines 9 and 10 and of the wash pumps 11 and 12 is decoupled by the valve 2 from the volume of the dilutor 1, the dilutor line 3, the load loop 6 and the hollow needle 5. The load loop 6 can now be made from a rigid material, for example from a solid plastic or metal, and as a tube for example, or, as has been described above, from one or more workpieces that have a number of suitable bores. The dosing accuracy and reproducibility are improved in this way, since these two aspects are not negatively affected by a large dead volume or by flexible and soft lines.

In known sample deposition devices, one of the most important reasons for sample contamination is the fact that sample is sucked into the syringe and that the sample volume present in the needle is likewise sucked into the syringe during washing. By means of several plunger strokes, the sample is then washed out, but this simply results in a dilution series. The spindle that moves the syringe plunger can have a small pitch, which affords an advantage in the movement of the syringe plunger. However, the quantity of washing solvent with which the syringe is cleaned is dependent on the strokes of the syringe plunger.

That is to say, the more washing solvent that is to be used for cleaning, the more strokes that have to be executed by the syringe plunger. However, a correspondingly high number of strokes increases the wear on the syringe.

The device according to the invention is constructed in such a way that existing apparatuses can also be retrofitted at reasonable outlay. The structure and the construction ensure that sample does not enter the dilutor 1 and that, with a sufficient amount, in principle any desired amount, of aqueous and/or organic washing solution, the sample-contaminated area in the needle 5 (hollow needle 5), in the load tube 6 (load loop 6) and in the injection valve 22 can be washed rapidly and simply, and that the needle 5 is positioned optimally in the injection port 21.

Compared to the Prior Art:
the dilutor 1 is decoupled from the needle 5,
the needle 5 is connected to a load tube 6 and has its own support, the contaminated area is washed via a T-piece 7 between dilutor 1 and load tube 6, and
the contamination area comprises only the injection valve 22, the injection port 21, the needle 5 and now the load tube 6, but no longer the dilutor 1.

By means of the dilutor 1 being decoupled from the needle 5 and turned through 180° for example, any air bubbles that are present do not remain in the syringe.

The needle 5 is connected to the load tube 6 by a union nut and fixed in the needle adapter 4.

The needle adapter 4 springs the needle 5 minimally, such that the needle 5 can be positioned in the injection port 21 at the abutment.

By virtue of its volume, the load tube 6 prevents sample from entering the dilutor 1. The volume of the load tube 6 (needle 5 to wash outlet T-union 7) is ca. 1.5 times the dilutor volume.

The valve 2 (here a check valve 2) decouples the wash lines 9 and 10 from the dilutor 1, from the load tube 6 and from the needle 5. The dosing accuracy of the dilutor 1 is not impaired by the volume and possible air bubbles in the wash lines 9 and 10.

The first connection element wash inlet T-union 8, which is positioned directly on the check valve 2, permits rapid changing of the two wash eluents.

During washing, the sample is not pushed to and fro by the plunger stroke of the dilutor 1, and instead is ejected by means of the wash pumps 11 and 12 via check valve 2 and wash outlet T-union 7.

The wash and waste module (wash module 15) can be positioned at the level of and close to the injection port 21. By virtue of the wash pumps 11, 12, no static pressure is needed for the washing. It is possible to use standard 1 or 2 liter wash eluent bottles.

The needle typically has a 22/22 gauge or other commercially available dimensions.

An injection cycle normally comprises a prewash macro, an injection macro and a clean macro. Moreover, an initiate macro is also needed in order to fill the dilutor, all the lines and wash ports.

With the initiate macro, the dilutor 1 is wetted and filled. For this purpose, the needle 5 is in waste position 16. While wash pump 12 is active, suction is performed with the dilutor 1, the speed of the plunger stroke having to be slower than the delivery rate of the wash pump. Thereafter, the dilutor 1 is ejected and the same procedure is repeated with wash pump 11. The dilutor 1 is then filled with water. Thereafter, wash 19 is overfilled with wash eluent 14 (organic) and then wash 18 is overfilled with wash eluent 13 (aqueous).

In the prewash macro, the needle is positioned in the injection port 21, while the injection valve 22 remains in inject position. Thereafter, wash pump 11 is briefly activated (ca. 5 seconds). The needle 5 is then drawn out from the injection port 21 and the dilutor sucks in 1 µl of air.

To ensure that the sample solution reaches the analysis system in the purest possible state, the effective sample volume is enclosed in the hollow needle 5 by a selectable pre-run segment (front volume) and a selectable after-run segment (rear volume) before and after heating of the sample volume. The front volume prevents diluted sample from being separated from the sample volume that is to be injected. The rear volume ensures that no air or system liquid at the end of the sample volume to be injected enters the analysis system. In the injection macro, the needle 5 moves into the sample bottle 20 and sucks in sample. The volume is obtained from the applied front volume plus injection volume plus rear volume (e.g. 5 µl+10 µl+10 µl; µl=microliter). The volumes can be varied depending on the amount of sample, the size of the load loop and the injection quantity.

With small amounts of sample, it would also be possible for the front volume and the rear volume, decoupled by small air bubbles, to be taken from wash 18. After the sample has been suctioned in, air can be suctioned in. The suctioned air volume can in principle be determined by the user and is, for example, 3 µl. The needle then travels briefly and fully into wash 18 position, in order to wash the needle 5 on the outside. The needle 5 then positions itself in the injection port 21. Before the injection valve 22 is turned to Load, the front volume (e.g. 5 µl) is ejected, after which the injection volume is forced into the loop 24 and the injection valve 21 is turned to inject position (start signal out). Thereafter, the dilutor 1 is fully ejected.

In the clean macro, the needle 5 remains in the injection port 21, and wash pump 12 (organic) is activated (ca. 2 to 5 times the dilutor volume). Thereafter, the needle 5 moves to wash 19 position, and wash pump 12 (organic) is activated again (ca. 100 µl). Thereafter, the needle 5 moves to the waste position 16, and wash pump 11 is activated. After ca. 2 times the dilutor volume, the needle 5 moves to wash 18 position. As soon as the needle 5 is in the wash position 18, the wash pump 11 is switched on again, and about 2 more dilutor volumes are pumped (end of the injection cycle).

While the wash pumps 11, 12 are active, the dilutor plunger could be drawn back slightly, in which case the suction speed must be slower than the delivery rate of the wash pumps. The ejection could then take place rapidly. With this plunger movement, the eluent in the dilutor is renewed. During the injector port cleaning phase, the needle 5 could also be drawn back by ca. 1 mm, in order to achieve better cleaning of the port.

Figure 5:
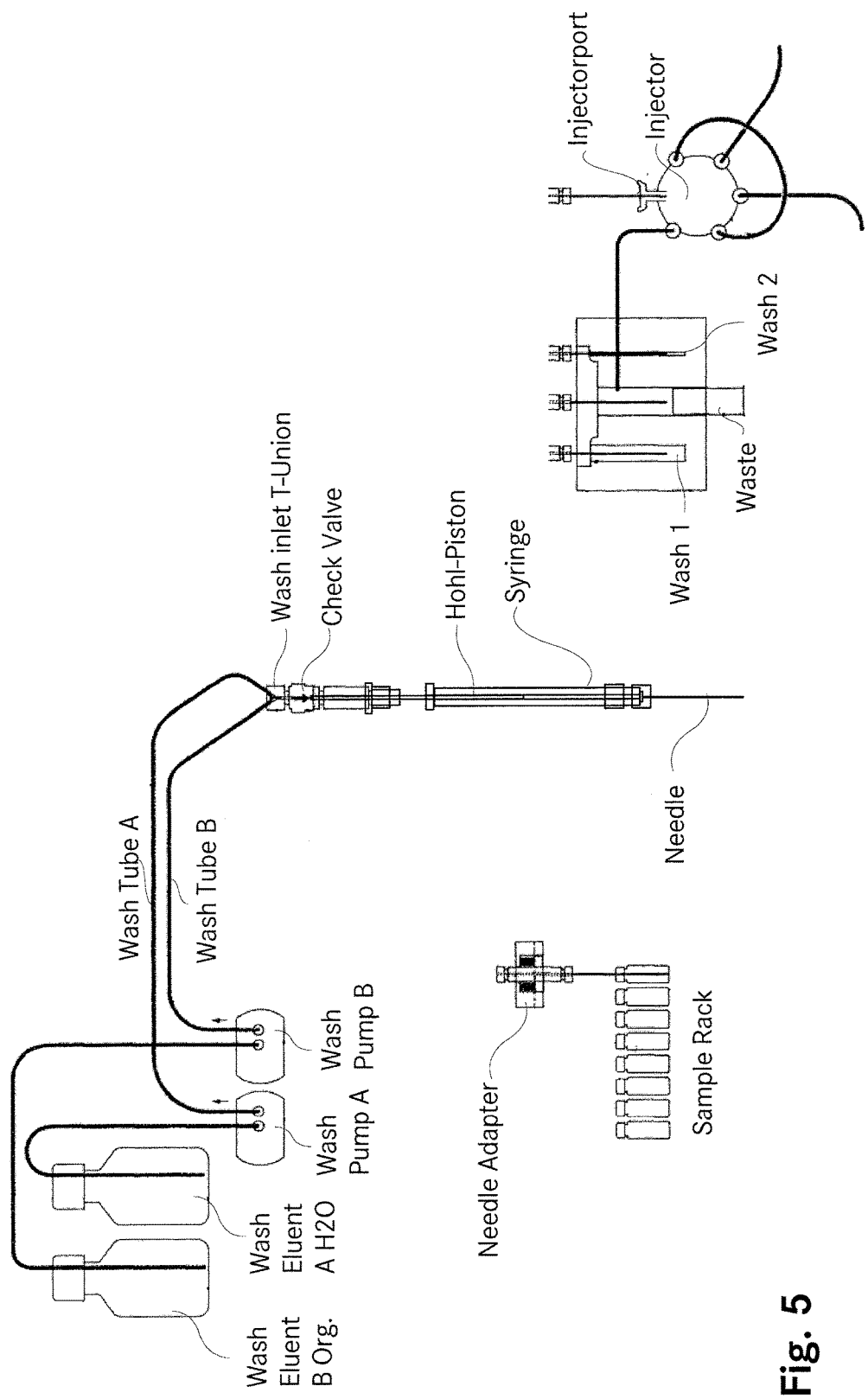
FIG. 5 shows a schematic view of a third illustrative embodiment of a device according to the invention.

FIG. 5 shows a third illustrative embodiment of a device according to the invention, in which the syringe (dilutor) and the hollow needle are not separated, and a connection element (T-piece) is provided only at the input, not at the output, of the check valve. Instead of the standard syringe, a syringe with a hollow piston is used. The wash inlet T-union and check valve are then located at the inlet of the hollow piston. The cleaning then also takes place from behind, i.e. from the container or containers with washing liquid via wash inlet T-union, check valve, syringe with hollow piston and through the needle.

It will be noted in conclusion that the invention makes available a device for collecting a sample and for depositing the sample in a sample-receiving port of a measuring apparatus, which device is particularly robust as regards reproducibility and contamination. The device according to the invention is also distinguished by a particularly simple and compact structure.

The invention claimed is:

1. A device for collecting a sample and for depositing the sample in a sample-receiving port of a measuring apparatus comprising a movable support with a hollow needle for collecting and depositing the sample and a dosing device, which is connected to the hollow needle, wherein the hollow needle and the dosing device are spatially fixed relative to one another and wherein a non-flexible line is provided between the hollow needle and the dosing device.

2. The device according to claim 1, wherein the non-flexible line is a load-loop.

3. The device according to claim 1, wherein the non-flexible line is designed to be exchangeable.

4. The device according to claim 1, wherein the non-flexible line is made of a rigid plastic or of a metal.

5. The device according to claim 1, wherein the non-flexible line is formed by one or more bores in a solid element made of metal or plastic.

6. The device according to claim 1, wherein said dosing device is connected to said non-flexible line by means of a dilutor line.

7. The device according to claim 6, wherein said dilutor line is formed as bore in a solid element made of metal or plastic.

8. The device according to claim 1, wherein a second connection element is arranged between and connected with said non-flexible line and said dosing device, said second connection element further being connected with a first connection element, wherein a first lead line for a first washing liquid is connected via a first pump, and a second lead line for a second washing liquid is connected via a second pump to the first connection element.

9. The device according to claim 8, wherein a valve is arranged between said first connection element and said second connection element.

10. The device according to claim 8, wherein said first connection element and said second connection element are T-pieces with three fluid connections.

* * * * *